United States Patent [19]

Roe et al.

[11] Patent Number: 5,624,426
[45] Date of Patent: Apr. 29, 1997

[54] DIAPER HAVING AN IMPROVED LEG CUFF

[75] Inventors: Donald C. Roe, West Chester; Kimberly A. Dreier, Cincinnati, both of Ohio

[73] Assignee: The Procter & Gamble Company, Cincinnati, Ohio

[21] Appl. No.: 642,738

[22] Filed: May 3, 1996

[51] Int. Cl.$^6$ .................................................. A61F 13/15
[52] U.S. Cl. ...................................... 601/385.2; 604/385.1
[58] Field of Search .............................. 604/385.1, 385.2, 604/386, 387, 391–402, 369

[56] References Cited

U.S. PATENT DOCUMENTS

| | | | |
|---|---|---|---|
| 4,490,148 | 12/1984 | Beckeström | 604/385 |
| 4,695,278 | 9/1987 | Lawson | 604/385.2 |
| 4,738,677 | 4/1988 | Foreman | 604/385.2 |
| 4,795,452 | 1/1989 | Blaney et al. | 604/385.1 |
| 4,808,177 | 2/1989 | DesMarais et al. | 604/385.1 |
| 5,061,261 | 10/1991 | Suzuki et al. | 604/385.2 |
| 5,080,658 | 1/1992 | Igaue et al. | 604/385.2 |
| 5,246,437 | 9/1993 | Minetola et al. | 604/385.2 |
| 5,476,458 | 12/1995 | Glaug et al. | 604/385.2 |

FOREIGN PATENT DOCUMENTS

| | | | |
|---|---|---|---|
| 2699813 | 7/1994 | France | 604/385.2 |
| 3-186262 | 8/1991 | Japan | 604/385.2 |
| 4-325153 | 11/1992 | Japan | 604/385.2 |
| 2216393 | 10/1989 | United Kingdom . | |

*Primary Examiner*—John G. Weiss
*Assistant Examiner*—K. M. Reichle
*Attorney, Agent, or Firm*—David M. Weirich; Steven W. Miller; Jacobus C. Rasser

[57] ABSTRACT

The present invention provides a disposable absorbent article including a topsheet, a backsheet, and an absorbent core having a pair of opposed longitudinal edges. The absorbent article includes a leg cuff extending at least laterally outwardly from each opposed longitudinal edge. Each leg cuff has a proximal edge, a distal edge and an elasticized region disposed between the proximal edge and the distal edge. The elasticized region has an inner edge, an outer edge and a width. The proximal edge of each leg cuff extends generally longitudinally along and adjacent to at least a portion of one of the opposed longitudinal edges and the distal edge of each of said leg cuffs is disposed laterally outwardly from the proximal edge. Each leg cuff includes an inner bond disposed adjacent at least a portion of the proximal edge of each leg cuff. An outer bond is spaced laterally outwardly from the inner bond, the spacing between the inner bond and said outer bond defining a leg cuff base width. Each leg cuff also includes an inner wall that extends upwardly and laterally outwardly from the inner bond to the inner edge of the elasticized region having a first height, and an outer wall that extends upwardly and laterally inwardly from the outer bond to the outer edge of the elasticized region having a second height. An elastic element is disposed in the elasticized region of each leg cuff and is provided generally parallel to the wearer's skin.

18 Claims, 3 Drawing Sheets

DIAPER HAVING AN IMPROVED LEG CUFF

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles having stand-up leg cuffs with wide elasticized skin-contacting surfaces which provide improved fit and containment characteristics.

BACKGROUND OF THE INVENTION

The major function of absorbent articles such as disposable diapers and adult incontinent briefs, is to absorb and contain body exudates. Such articles are also intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article. This is most evident with loose fecal material which is not easily absorbed by the absorbent article and tends to "float" on the top surface of the absorbent article.

Disposable diapers, such as those disclosed in U.S. Pat. No. 3,860,003 issued to Kenneth Barclay Buell on Jan. 14, 1975, generally have topsheet, a backsheet, an absorbent core, and elasticized leg flaps that improve the diaper's ability to contain body exudates. However, despite the effectiveness of such structures, body exudates can leak through the leg flaps and soil the wearer's clothing because the diaper does not constrain the free flow of such material or provide a structure to hold it within the diaper so that as such material flows freely on the surface of the topsheet, it tends to work its way past the elasticized leg flaps. To improve the containment characteristics of diapers numerous different leg cuff configurations have been identified. An example of an absorbent comprising leg cuffs with improved containment characteristics are described in U.S. Pat. No. 4,808,177 issued to DesMarais et al. on Feb. 28, 1989. These elasticized leg cuffs prove effective generally to prevent wicking and overflow from the fluid laden diaper to clothing contacting the edges of the diaper in that the elasticized leg cuffs present a liquid impervious barrier between the edge of the diaper and the contacting clothing, and in addition, provide a gasketing action about the legs of the wearer. However, such elasticized leg cuffs have the tendency to indent and mark the skin because the elastic force is concentrated along a narrow elastic band, resulting in high localized pressures. Although attempts have been made to address the problem of skin marking by utilizing wider elastics in the leg cuffs to reduce localized pressure where the cuffs contact the skin of the wearer, such attempts have not been completely successful. Because the distal edge of the cuff is not controlled, if the diaper is put on incorrectly or if the wearer moves, the elastics may be displaced from their optimum position for containment and comfort and the wide surface of the elastics may be presented at an angle or perpendicular to the skin. This results in the elastic force being concentrated at the edge of the elastic (or at the folded edge should the elastomeric buckle) rather than spread across the wide surface of the elastic. As such, the effectiveness of the cuff and its comfort may be substantially decreased leading to skin marking and irritation.

Therefore, it is an object of the present invention to provide an absorbent article which has improved comfort and containment characteristics.

It is also an object of the present invention to provide an absorbent article having a standing cuff which acts as a restraint against the leakage of body exudates without marking or irritating the skin of the wearer.

A further object of the present invention is to provide standing elasticized leg cuffs having a wide elasticized skin-contacting surface.

Yet another object of the present invention is to provide elasticized leg cuffs wherein the edges of the wide elasticized region are controlled.

A still further object of the present invention is provide a wide elasticized skin-contacting surface which is presented parallel to the wearer's skin throughout the dynamic range of baby motions.

SUMMARY OF THE INVENTION

The present invention provides a disposable absorbent article to be fitted to a wearer having a front waist region, a rear waist region, a crotch region disposed between the front waist region and the rear waist region, a longitudinal centerline and a lateral centerline. The absorbent article includes a topsheet, a backsheet joined with the topsheet, and an absorbent core disposed between the topsheet and the backsheet, the absorbent core having a pair of opposed longitudinal edges.

The absorbent article also includes a leg cuff extending at least laterally outwardly from each opposed longitudinal edge. Each leg cuff preferably has an inner surface and an opposed outer surface, a proximal edge, a distal edge and an elasticized region disposed between the proximal edge and the distal edge. The elasticized region has an inner edge, an outer edge disposed laterally outwardly from the inner edge and a width of between about 3 mm and about 15 min. The proximal edge of each leg cuff preferably extends generally longitudinally along and adjacent to at least a portion of one of the opposed longitudinal edges. The distal edge of each of said leg cuffs is preferably disposed laterally outwardly from the proximal edge.

Each leg cuff preferably includes an inner bond disposed adjacent at least a portion of the proximal edge of each leg cuff. The inner bond preferably joins the leg cuff to the underlying structure of the absorbent article. An outer bond is spaced laterally outwardly form the inner bond, the spacing between the inner bond and the outer bond defining a leg cuff base width. The outer bond preferably joins at least a portion of the leg cuff adjacent the distal edge to the absorbent article.

An inner wall of each leg cuff extends upwardly and laterally outwardly from the inner bond to the inner edge of the elasticized region. The inner wall has a first height of between about 30 mm and about 80 mm. An outer wall which extends upwardly and laterally inwardly from the outer bond to the outer edge of the elasticized region. The outer wall has a second height of between about 15 mm and about 50 mm.

An elastic element is preferably disposed in the elasticized region of each leg cuff. The elasticized region of the leg cuff is preferably provided generally parallel to the wearer's skin when the absorbent article is fitted to the wearer.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, and the like.

Figure 1:
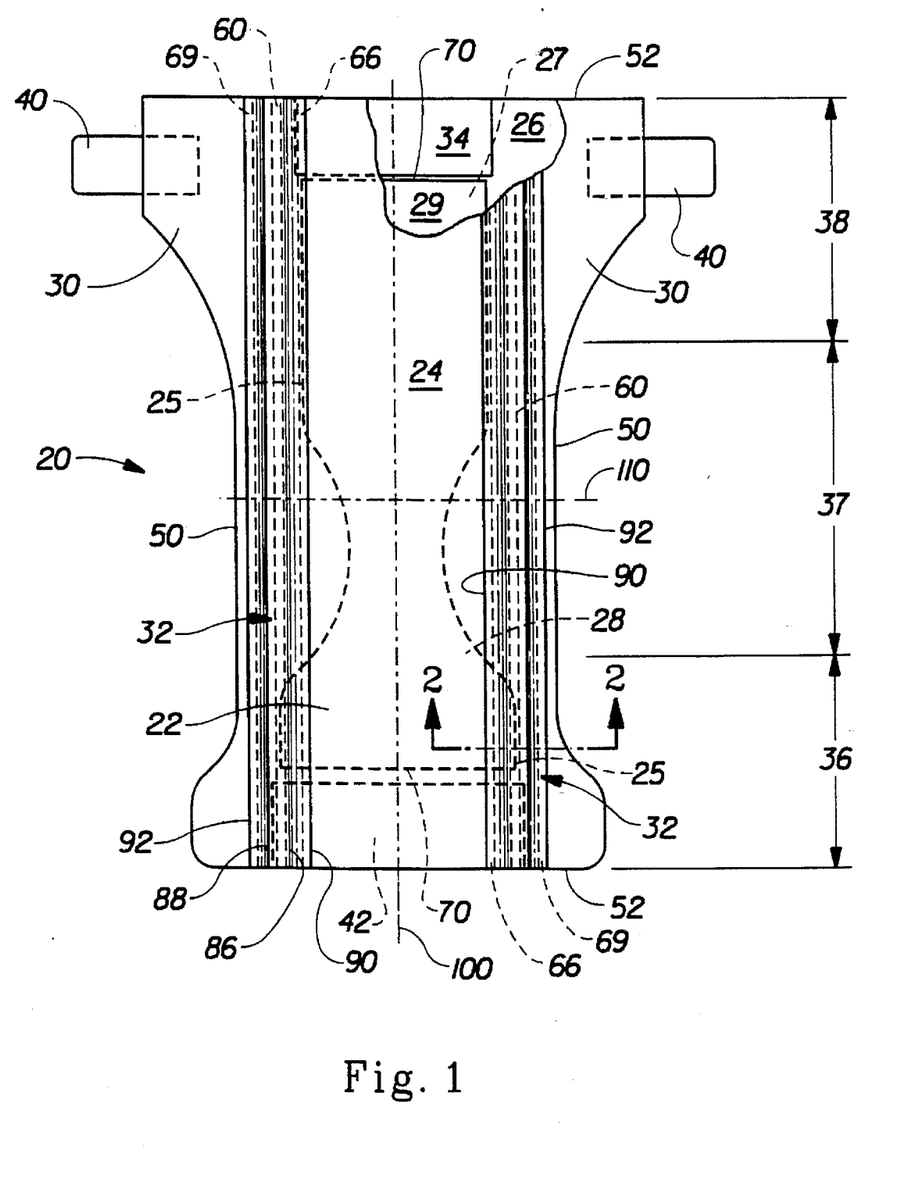
FIG. 1 is a plan view of an absorbent article embodiment of the present invention having portions cut away to reveal the underlying structure, the body-facing surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26; side panels 30; elasticized leg cuffs 32; an elastic waist feature 34; and a fastening system including at least one engaging component 40 and at least one landing component 42. The diaper 20 is shown in FIG. 1 to have a first waist region 36, a second waist region 38 opposed to the first waist region 36, a crotch region 37 positioned between the first waist region 36 and the second waist region 38, and a periphery which is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993; each of which is incorporated herein by reference.

Figure 2:
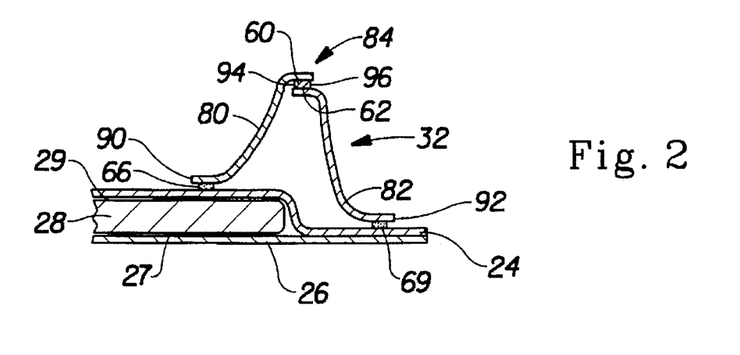
FIG. 2 is a fragmentary cross-sectional view taken along section line 2—2 of FIG. 1.

FIG. 2 is a fragmentary cross-sectional view of the diaper 20 taken along section line 2—2 of FIG. 1. The containment assembly 22 of the diaper 20 is shown in FIG. 1 as comprising the main body (chassis) of the diaper 20. The containment assembly 22 comprises at least an absorbent core 28 and preferably an outer covering layer comprising the top sheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has longitudinal edges 25, a garment surface 27 and a body surface 29. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28, however, should be compatible with the design loading and the intended use of the diaper 20. Further, the size and absorbent capacity of the absorbent core 28 may be varied to accommodate wearers ranging from infants through adults. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 emitted "Absorbent Articles With Dual-Layered Cores" issued to Weisman et al. on Jun. 16, 1987; U.S. Pat.

No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 26 is preferably impervious to liquids (e.g., urine) and is preferably manufactured from a thin plastic film, although other flexible liquid impervious materials may also be used. (The term "flexible" refers to materials which are compliant and will readily conform to the general shape and contours of the human body.) The backsheet 26 prevents the exudates absorbed and contained in the absorbent core 28 from wetting articles which contact the diaper 20 such as bedsheets and undergarments. Thus, the backsheet 26 may comprise a woven or nonwoven material, polymeric films such as thermoplastic films of polyethylene or polypropylene, or composite materials such as a film-coated nonwoven material. Preferably, the backsheet is a thermoplastic film having a thickness of about 0.012 mm (0.5 mil) to about 0.051 mm (2.0 mils). Particularly preferred materials for the backsheet include blown films and cast films as manufactured by Tredegar Industries, Inc. of Terre Haute, Ind., under the trade names RR8220 and RR5475, respectively. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The backsheet 26 may be elastically extensible in one or more directions. In one embodiment, the backsheet 26 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the U.S. Pat. No. 5,518,801 entitled "Web Materials Exhibiting Elastic-Like Behavior" issued to Chappell, et al. on May 21, 1996 (PCT Publication No. WO 95/03765 published Feb. 9, 1995), which is incorporated herein by reference. In alternate embodiments, the as backsheet 26 may comprise elastomeric films, foams, strands, or combinations of these or other suitable materials with nonwovens or synthetic films.

The backsheet 26 is positioned adjacent the garment surface 27 of the absorbent core 28 and is preferably joined thereto by attachment means such as those well known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. More preferably the attachment means will include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The topsheet 24 is positioned adjacent the body surface 29 of the absorbent core 28 and is preferably joined thereto and to the backsheet 26 by attachment means such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28.

The topsheet 24 is preferably compliant, soft feeling, and non-irritating to the wearer's skin. Further, the topsheet 24 is preferably liquid pervious, permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbond, carded, wet-laid, meltblown, hydroentangled, combinations of the above, or the like. One preferred topsheet 24 comprises a web of staple length polypropylene fibers such as is manufactured by Veratec, Inc., a Division of International Paper Company, of Walpole, Mass. under the designation P-8.

The diaper 20 preferably further comprises an elastic waist feature 34 that provides improved fit and containment. The elastic waist feature 34 is that portion or zone of the diaper 20 which is intended to elastically expand and contract to dynamically fit the wearer's waist. The elastic waist feature 34 at least extends longitudinally outwardly from at least one of the waist edges 70 of the absorbent core 28 and generally forms at least a portion of the end edge 52 of the diaper 20. Disposable diapers are generally constructed so as to have two elastic waist features, one positioned in the first waist region 36 and one positioned in the second waist region 38, although diapers can be constructed with a single elastic waist feature. Further, while the elastic waist feature 34 or any of its constituent elements can comprise a separate element affixed to the diaper 20, the elastic waist feature 34 is preferably constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985 and the above referenced U.S. Pat. No. 5,151,092 issued to Buell on Sep. 9, 1992; and U.S. Pat. No. 5,221,274 issued to Buell on Jun. 22, 1993; each of these references being incorporated herein by reference.

The diaper 20 preferably also comprises a fastening system. The fastening system preferably maintains the first waist region 36 and the second waist region 38 in an overlapping configuration so as to provide lateral tensions about the circumference of the diaper 20 to hold the diaper 20 on the wearer. The fastening system preferably comprises tape tabs and/or hook and loop fastening components. In one preferred embodiment, as shown in FIG. 1, the fastening system includes engaging components 40 disposed in said second waist region 38 generally along said longitudinal edges 50 of the diaper and landing zone 42 disposed in the front waist region 36 adjacent said end edge 52. (As used herein, the term "disposed" is used to mean that an element (s) of the diaper is formed (joined and positioned) in a particular place or position as a unitary structure with other elements of the diaper or as a separate element joined to another element of the diaper.) Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946, 527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. 4,662,875 B1 entitled "Absorbent Article" issued to Hirotsu et al. on May 5, 1987; and the hereinbefore referenced U.S. Pat. No. 5,151,092 issued to Buell on Sep. 9, 1992; and U.S. Pat. No. 5,221,274 issued to Buell on Jun. 22, 1993; each of which is incorporated herein by reference.

The diaper 20 may also comprise side panels 30. The side panels 30 may be elastic or extensible to provide a more comfortable and contouring fit by initially conformably fitting the diaper to the wearer and sustaining this fit throughout the time of wear well past when the diaper has been loaded with exudates since the elasticized side panels 30 allow the sides of the diaper to expand and contract. The side panels 30 may also provide more effective application of the diaper 20 because even if the diaperer pulls one elasticized side panel 30 farther than the other during application (asymmetrically), the diaper 20 will "self-adjust" during wear.

While the diaper 20 of the present invention preferably has the side panels 30 disposed in the second waist region 38; the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. Pat. No. 5,151,092 issued to Buell on Sep. 9, 1992; and U.S. Pat. No. 5,221,274 issued to Buell on Jun. 22, 1993; U.S. patent application Ser. No. 08/155,048 entitled "Absorbent Article With Multi-Directional Extensible Side Panels" filed Nov. 19, 1993 in the names of Robles, et al.; each of which are incorporated herein by reference.

The diaper 20 preferably further comprises leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

In preferred embodiments, the leg cuffs 32 extend generally longitudinally from the from waist region 36 through the crotch region 37 to the rear waist region 38. Although the cuffs 32 may extend from one end edge 52 of the diaper 20 to the opposite end edge 52, it is not necessary that they do so. Further, although the cuffs 32 are preferably structurally mirror images of each other, the cuffs 32 may be configured differently. In any case, preferably one leg cuff 32 extends laterally outwardly from each longitudinal edge of the core 25. It is also preferred that at least a portion of each leg cuff 32 is bonded sealed or joined in or adjacent the front waist region 36 and the rear waist region 38 to prevent any liquids that may pass through the inner wall 80 of the cuff 32 from channeling along the interior of the leg cuff 32 and being directed out of the diaper 20 in the front or rear waist regions 36 and 38.

Figure 3:
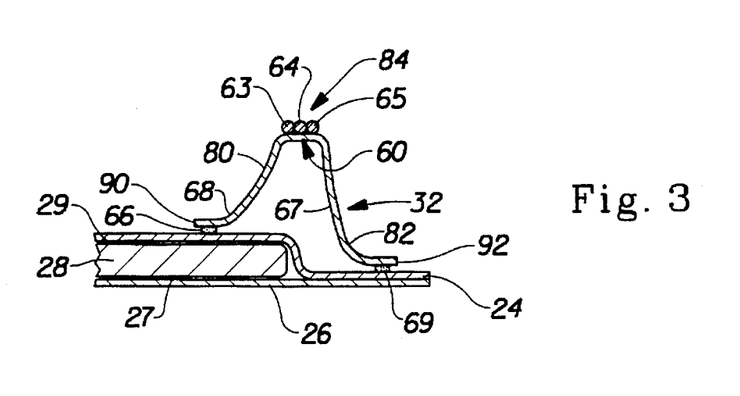
FIG. 3 is a fragmentary cross-sectional view of an alternative embodiment of the invention.
Figure 4:
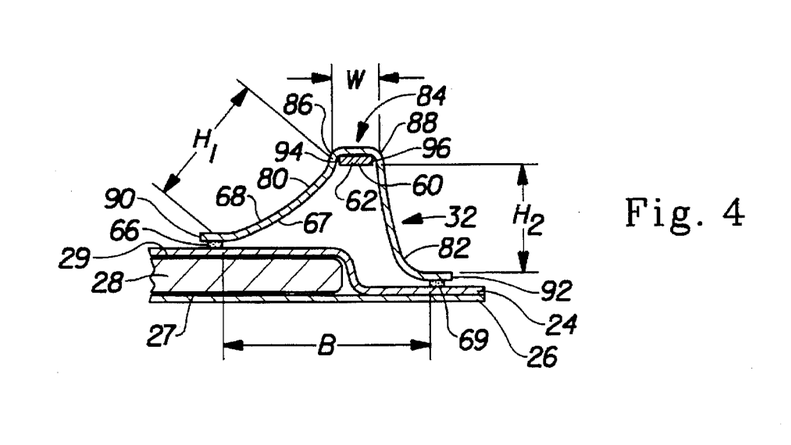
FIG. 4 is a fragmentary cross-sectional view of one embodiment of the cuff of the present invention.

With reference to FIGS. 2–6 the leg cuffs 32 of the present invention each have a proximal edge 90 and a distal edge 92. Each proximal edge 90 extends generally longitudinally along and adjacent to at least a portion of one of the longitudinal edges 25 of the absorbent core 28. The distal edge 92 of each leg cuff 32 is disposed laterally outwardly of its corresponding proximal edge 90. (As used herein, the terms "laterally inboard" or "laterally inwardly" refer to relative locations which are closer to the longitudinal centerline 100 than another location to which the laterally inboard location is being compared. The terms "laterally outboard" or "laterally outwardly" refer to relative locations that are farther away from the longitudinal centerline 100 of the diaper 20 than other locations to which the laterally outboard location is being compared.) Each leg cuff 32 comprises an inner wall 80, an outer wall 82, and a generally flat elasticized region 84 that spans between the inner wall 80 and the outer wall 82 defining a width W. The elasticized region 84 has an inner edge 86 and an outer edge 88. The inner wall 80 is that portion of the leg cuff 32 which extends upwardly away from the chassis 22 of the diaper 20 and laterally outwardly from the inner bond 66 to the elasticized region 84 of the leg cuff 32 when the cuff 32 is in a contracted, stand-up configuration. The outer wall 82 extends upwardly away from the chassis 22 of the diaper 20 and laterally inwardly from the outer bond 69 to the elasticized region 84 of the leg cuff 32 when the cuff 32 is in a contracted, stand-up configuration. As shown in FIG. 4, the length (or height) H1 of the inner wall 80 is measured from the bond 66, which joins the inner wall 80 to the underlying structure of the diaper 20, to the inner edge 86 of the elasticized region 84. The length (or height) H2 of the outer wall 82 is measured from the outer bond 69, which joins the outer wall 82 to the underlying structure of the diaper 20, to the outer edge 88 of the elasticized region 84.

Although an approximation of the length H1 and H2 can be obtained by measuring the leg cuff 32 as it stands up in normal use, a more accurate measurement may be obtained by removing the cuff 32 from the diaper 20 and placing it flat on a relatively planar surface before measuring the length H1 and H2. Relative to one another, the inner wall 80 of each leg cuff 32 is preferably disposed laterally inwardly of the corresponding outer wall 82, as shown in FIGS. 2–6. It should be noted, however, that embodiments are contemplated wherein at least a portion of the inner wall 80 may be disposed laterally outwardly from at least a portion of the corresponding outer wall 82.

Figure 5:
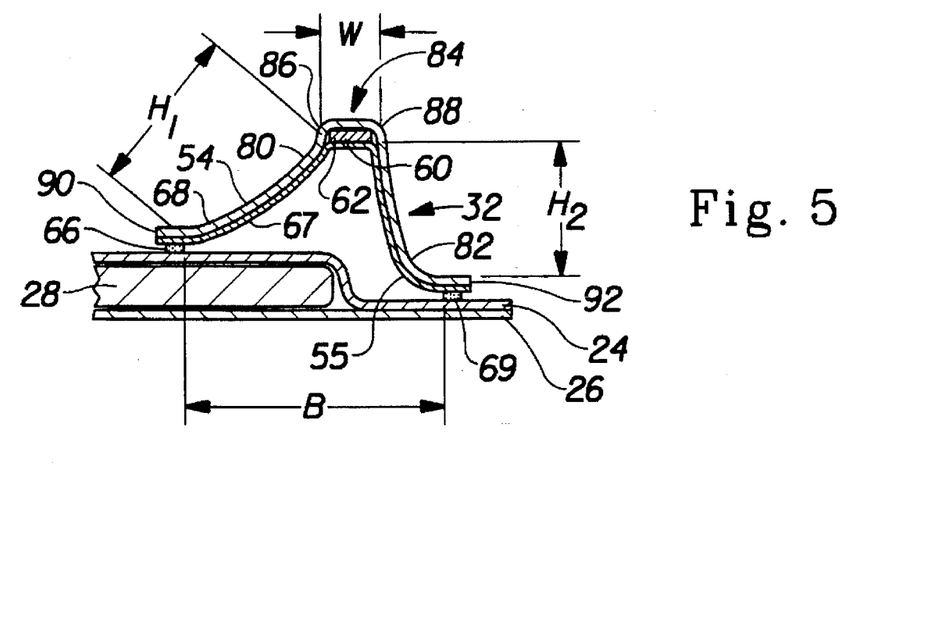
FIG. 5 is a fragmentary cross-sectional view of one embodiment of the cuff of the present invention.

The leg cuffs 32 may comprise a single lamina or may comprise a laminate of more than one lamina. The laminae may be generally coextensive or may be of different size or shape. Further, the lamina may be directly or indirectly joined to each other with continuous or intermittent bonding means as are known in the art. One example of a leg cuff 32 comprising a laminate of more than one lamina is shown in FIG. 5. First laminate 54 is shown to be generally coextensive with second laminate 55. Elastic element 60 is shown to be disposed between the laminae, however, embodiments are contemplated wherein the elastic element 60 is disposed and/or joined to either surface of the first laminate 54 or the second laminate 55.

The materials that make up the inner and outer walls, 80 and 82, of the leg cuffs 32 preferably comprise soft, compliant, air-permeable, hydrophobic materials such as nonwovens, formed films, microporous films, or foams. One preferred material is a hydrophobic polypropylene nonwoven having a basis weight of 20 grams per square yard, available from Veratec, Inc. of Walpole, Mass. under the trade designation P-8. In one embodiment, the inner wall 80 and the outer wall 82 comprise different materials.

The leg cuffs 32 are maintained in their stand-up configuration, away from the chassis 22 of the diaper 20 by an elastic element 60, as shown in FIGS. 2–6. (Although inelastic means may be utilized to provide the leg cuffs 32 in their stand-up configurations, such means are less desirable than elastomeric means due to the fact that inelastic means will generally not be able to conform as well to the body of the wearer as elastomeric means, especially when the wearer moves. As used herein, the term "elastomeric" refers to materials which extend in at least one direction when a stretching force is applied to the material, and then return to approximately their original dimensions after the force is removed.) The elastic element 60 may comprise any one or more elastomeric materials as are known in the art, including rubber or synthetic rubber, elastomeric "KRATON"-based films, other elastomeric films, elastomeric foams as well as any other known elastomeric materials or combinations thereof. One exemplary elastomeric material is a strand of woven material comprising 12% "LYCRA" and 88% nylon manufactured by Rainwood Corp. of Tupelo, Miss.

Each elastic element 60 preferably comprises a single elastomeric member 62, however, multiple elastomeric members 64 may be used. One example of multiple elastomeric members 64 is shown in FIG. 3. In multiple elastomeric member embodiments, the elastomeric members 64 may be joined to each other or may remain separate members. Further, the elastic element 60 may extend throughout the entire length of the cuff 32 or may be limited to specific portions of the cuff 32. In preferred embodiments, the elastic element 60 is configured such that at least the portion of the cuffs 32 disposed in the crotch region 37 stands up away from the underlying structure of the diaper 20 while in use.

The elastomeric member(s) 62 or 64 provide the elasticized region 84 of the leg cuff 32 with a width W. In embodiments including a single elastomeric member 62 the width W corresponds generally with the distance between the laterally inboard most edge 94 of the elastomeric member 62 and the laterally outboard most edge 96 of the elastomeric member 62. In multiple elastomeric member embodiments, the width W generally corresponds to the distance between the laterally inboard most elastic 63 and the laterally outboard most elastic 65, as shown in FIG. 3. In any embodiment, the width W is preferably between at least about 3 mm and about 15 mm. More preferably, width W is between about 5 mm and about 8 mm. It has been found that such widths help to distribute the forces provided by the elastomeric member(s) 62, 64 over a relatively wider region than conventional leg cuffs 32 without providing any additional irritation to the wearer. Thus, the overall comfort of the article is improved and the possibility and extent of red marking is reduced.

The length (or height) of the inner and outer walls 80 and 82 have been found to be important in order to allow the elastic element 60 to conform to the shape and curvature of the wearer's body while maintaining the elasticized region 84 of the leg cuff 32 in an orientation parallel to the wearer's skin. It is desirable to maintain the elasticized region 60 parallel to the skin of the wearer throughout the time the diaper 20 is being worn to improve the containment characteristics of the leg cuffs 32 and to reduce the likelihood and extent of marking generally associated with the leg cuffs 32 being in contact with the skin of the wearer. While it is recognized that the most desirable lengths for the inner and outer walls 80 and 82 of each cuff will vary depending on the wearer and the specific diaper design, in general, the length H1 of the inner wall 80 is preferably greater than the length H2 of outer wall 82. Preferably, the ratio of H1/H2 is between about 1.25 and 2.5, and more preferably between about 1.3 and about 2.0. In one preferred embodiment, each leg cuff inner wall 80 preferably has a length H1 which is between at least about 30 mm and about 80 mm and each leg cuff outer wall 82 preferably has a length H2 which is between at least about 15 mm and about 50 mm. More preferably, each leg cuff inner wall 80 has a length H1 between about 45 mm and about 65 mm and each leg cuff outer wall 82 preferably has a length H2 between about 25 mm and about 40 mm.

The leg cuffs 32 may be constructed in any number of suitable configurations. FIGS. 2–6 illustrate three different preferred configurations. In FIG. 2, the inner wall 80 comprises a separate material from that of the outer wall 82. The materials comprised in each wall are shown to be joined together in an overlapping configuration. In such configurations, the inner wall 80 and the outer wall 82 surround the elastic element 60. In a particularly preferred embodiment, as shown in FIG. 2, the elastic element 60 is disposed in the elasticized region 84 between the material comprised in the inner wall 80 and the material comprised in the outer wall 82. The overlapping materials may be reversed from the configuration shown in FIG. 2 in order to provide different containment and/or skin friendliness characteristics.

Alternatively, the elastic element 60, or any portion thereof, may be joined to the inner surface 67 or to the outer surface 68 of the cuff 32. In FIG. 3, the elastic element 60 comprising a plurality of elastic members 64 is disposed adjacent the outer surface 68 of the cuff 32. Although it may be desirable to join some or all of the elastic members 64 comprised in the elastic element 60, or portions thereof, it is not necessary to do so. Further, a single undivided material may make up the entire length of both the inner wall 80 and the outer wall 82, or any portion of the inner wall 80 and/or the outer wall 82. The whole elastic element 60 or any portion thereof may be wrapped in or covered with another material or materials. Such material(s) may reduce the possibility of delamination of the elastomeric from the cuff 32 in configurations where it is joined thereto.

Figure 6:
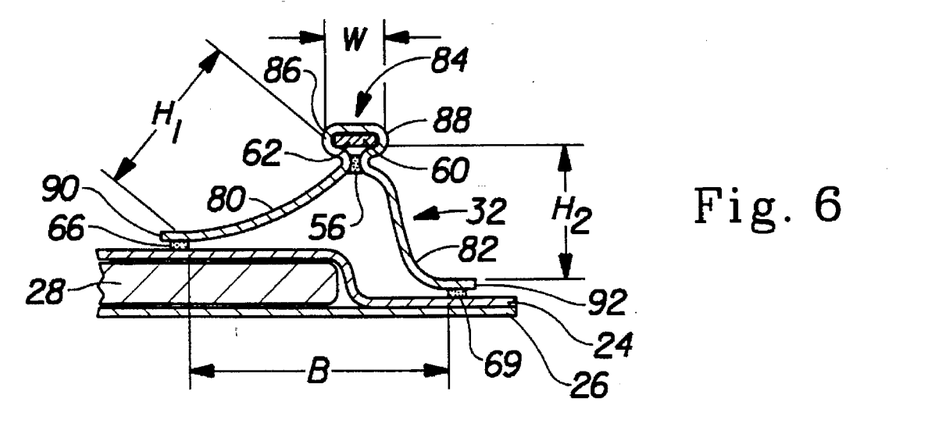
FIG. 6 is a fragmentary cross-sectional view of one embodiment of the cuff of the present invention.

As shown in FIG. 6, at least a portion of the inner wall 80 may be joined, directly or indirectly, to at least a portion of outer wall 82. In the embodiment shown, the inner wall 80 and the outer wall 82 completely surround the elastic element 60. The bond 56 which joins the inner wall 80 and the outer wall 82 may comprise any means known in the art, including those mentioned herein with regard to inner and outer bonds 66 and 69.

In any configuration, the cuff wall materials may be joined to each other or to the elastic element 60 by any means known in the art, including adhesives, ultrasonic bonding, heat, pressure or any other known bonding means or combination of bonding means. In preferred embodiments, an adhesive bond is employed. One exemplary adhesive is available from Findley Adhesives Corporation of Wauwatosa, Wis. under the trade designation Findley Adhesive 2031.

The inner and outer walls 80 and 82 may also be joined to the underlying structure of the diaper 22 by any joining means known in the art, including those mentioned herein. In one preferred embodiment, the inner bond 66 joins the inner wall 80 of the cuff 32 to the underlying structure of the diaper 20 laterally inboard of the longitudinal edge 25 of the core 28 and the outer bond 69 joins the outer wall 82 of the cuff 32 to the underlying structure of the diaper 20 laterally outboard of the longitudinal edge 25 of the core 28. However, embodiments are contemplated wherein the inner wall 80 is joined to the underlying structure of the diaper 20 laterally outboard of the longitudinal edge 25 of the core 28 and the outer wall 82 is joined to the underlying structure of the diaper 20 laterally outboard of the longitudinal edge 25 of the core 28, or wherein the inner wall 80 is joined to the underlying structure of the diaper 20 laterally inboard of the longitudinal edge 25 of the core 28 and the outer wall 82 is joined to the underlying structure of the diaper 20 laterally inboard of the longitudinal edge 25 of the core 28. In any case, the inner bond 66 is preferably disposed adjacent at least a portion of the proximal edge 90 of the leg cuff 32 and the outer bond 69 is spaced laterally outwardly form the inner bond 66. The distance between the bonds 66 and 69 defines the width of the base of the cuff 32, which is designated B (shown in FIG. 4).

As with the width W, and the length H1 and H2 of each inner and outer wall, 80 and 82, it has been found that the spacing B between the inner bond 66 and the outer bond 69 is an important factor contributing to the performance of each leg cuff 32. While the preferred spacing B between the bonds 66 and 69 is dependent on the particular inner and outer cuff wall heights (H1 and H2), generally the spacing B between the bonds 66 and 69 is increased as the wall length H1 and H2 are increased. In preferred embodiments wherein the length H1 of the inner walls 80 ranges between about 30 mm and about 80 mm the length H2 of the outer walls 82 ranges between about 15 mm and about 50 mm, B is preferably at least about 10 mm and more preferably at least about 15 mm.

The diaper 20 is preferably applied to a wearer by positioning one of the waist regions, preferably the second waist region 38, under the wearer's back and drawing the remainder of the diaper 20 between the wearer's legs. The other waist region, preferably the first waist region 36, is positioned across the front of the wearer. The diaperer then wraps the side panels 30 around the wearer such that the front waist region 36 and the rear waist region 38 are in an overlapping configuration. The side panels 30 will typically be extended and tensioned during this operation so as to conform to the size and shape of the wearer. The fastening system is secured to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article to be fitted to a wearer having a front waist region, a rear waist region, a crotch region disposed between said front waist region and said rear waist region, a longitudinal centerline and a lateral centerline, the absorbent article comprising:

a topsheet;

a backsheet joined with said topsheet;

an absorbent core disposed between said topsheet and said backsheet, said absorbent core having opposed longitudinal edges; and a leg cuff extending at least laterally outwardly from each one of said opposed longitudinal edges, each said leg cuff having an inner surface, an outer surface opposed to said inner surface, a proximal edge, a distal edge and an elasticized region disposed between said proximal edge and said distal edge, said elasticized region having an inner edge, an outer edge disposed laterally outwardly from said inner edge and a width of between about 3 mm and about 15 mm, each said proximal edge extending generally longitudinally along and adjacent to at least a portion of one of said opposed longitudinal edges, said distal edge of each respective leg cuff disposed laterally outwardly from said proximal edge of each said respective leg cuff, at least a portion of each said leg cuff comprising:

an inner bond disposed adjacent at least a portion of said proximal edge of each said leg cuff, said inner bond joining each said leg cuff to the absorbent article;

an outer bond spaced laterally outwardly from said inner bond, said spacing between said inner bond and said outer bond defining a leg cuff base width, said outer bond joining at least a portion of each said leg cuff adjacent said distal edge to the absorbent article, an inner wall extending upwardly and laterally outwardly from said inner bond to said inner edge of said elasticized region, said inner wall having a first height between about 30 mm and about 80 mm;

an outer wall extending upwardly and laterally inwardly from said outer bond to said outer edge of said elasticized region, said outer wall having a second height between about 15 mm and about 50 mm; and an elastic disposed in said elasticized region of each said leg cuff;

said elasticized region of each said leg cuff being provided generally parallel to the skin of the wearer when the absorbent article is fitted to the wearer.

2. The disposable absorbent article of claim 1 wherein said width of said elasticized region is between about 5 mm and about 8 mm.

3. The disposable absorbent article of claim 1 wherein said first height of said inner wall is between about 45 mm and about 65 mm.

4. The disposable absorbent article of claim 3 wherein said second height of said outer wall is between about 25 mm and about 40 mm.

5. The disposable absorbent article of claim 1 wherein a ratio of said first height of said inner wall to said second height of said outer wall is between about 1.25 and about 2.5.

6. The disposable absorbent article of claim 1 wherein a ratio of said first height of said inner wall to said second height of said outer cuff is between about 1.3 and about 2.0.

7. The disposable absorbent article of claim 1 wherein said leg cuff base width is at least about 10 mm.

8. The disposable absorbent article of claim 7 wherein said leg cuff base width is at least about 15 mm.

9. The disposable absorbent article of claim 1 wherein said elastic comprises at least two elastic members.

10. The disposable absorbent article of claim 9 wherein said elastic members are joined to each other.

11. The disposable absorbent article of claim 1 wherein at least a portion of each respective elastic is bonded to said inner surface of said each respective leg cuff in said elasticized region.

12. The disposable absorbent article of claim 1 wherein at least a portion of each respective elastic is bonded to said outer surface of said each respective leg cuff in said elasticized region.

13. The disposable absorbent article of claim 1 wherein at least a portion of said elastic is bonded between said inner wall and said outer wall.

14. The disposable absorbent article of claim 1 wherein said inner wall and said outer wall comprise the same material.

15. The disposable absorbent article of claim 1 wherein said inner wall and said outer wall comprise different materials.

16. The disposable absorbent article of claim 1 wherein each said leg cuff comprises a laminate of a first lamina and a second lamina.

17. The disposable absorbent article of claim 16 wherein at least a portion of said elastic is disposed between said first lamina and said second lamina.

18. The disposable absorbent article of claim 1 wherein at least a portion of said inner wall is joined with at least a portion of said outer wall such that said inner wall and said outer wall completely surround said elastic.

* * * * *